(12) United States Patent
Segal

(10) Patent No.: US 7,850,646 B2
(45) Date of Patent: Dec. 14, 2010

(54) SAFETY SYRINGE WITH RE-USABLE MAIN PARTS, METHOD FOR DISPOSAL OF A NEEDLE INTO A CONTAINER AND CONTAINER FOR DISPOSABLE PARTS

(75) Inventor: Alan Julian Segal, Cheshire (GB)

(73) Assignee: Astek Innovations Limited, Cheshire (GB)

( * ) Notice: Subject to any disclaimer, the term of this patent is extended or adjusted under 35 U.S.C. 154(b) by 1877 days.

(21) Appl. No.: 10/496,196

(22) PCT Filed: Nov. 29, 2002

(86) PCT No.: PCT/GB02/05398

§ 371 (c)(1), (2), (4) Date: Jul. 27, 2004

(87) PCT Pub. No.: WO03/047664

PCT Pub. Date: Jun. 12, 2003

(65) Prior Publication Data

US 2005/0124933 A1    Jun. 9, 2005

(30) Foreign Application Priority Data

Nov. 30, 2001  (GB) ................................ 0128691.3

(51) Int. Cl.
*A61M 5/00*   (2006.01)
(52) U.S. Cl. ...................... 604/110; 206/364
(58) Field of Classification Search .............. 604/110, 604/192–194, 197, 198; 206/364
See application file for complete search history.

(56) References Cited

U.S. PATENT DOCUMENTS

| 4,351,434 A | 9/1982 | Elisha |
| 4,425,120 A | 1/1984 | Sampson et al. |
| 4,600,112 A | 7/1986 | Shillington et al. |

(Continued)

FOREIGN PATENT DOCUMENTS

DE      39 03 974 A    8/1990

(Continued)

OTHER PUBLICATIONS

Canadian Examination Report dated Sep. 28, 2009 with respect to patent family member Canadian Patent Application No. 2,468,683.

*Primary Examiner*—Nicholas D Lucchesi
*Assistant Examiner*—Gerald Landry, II
(74) *Attorney, Agent, or Firm*—Greenblum and Bernstein, P.L.C.

(57) ABSTRACT

A syringe has a barrel to receive a cartridge. The barrel has a front end portion to which a needle is connected for engagement with the cartridge. At its rear end, the barrel has a plunger mechanism. A sleeve is slidably mounted on the barrel and can be pushed forwards to sheath the needle. The needle is mounted on the barrel via a push-fit mounting device. The needle can be removed for disposal in a container by inserting the syringe into a tube on top of the container so that the protective needle sleeve is pushed back and the needle and mounting device pass through a collar of gripping fingers at an inner end of the tube. The fingers catch behind the mounting device so that this is pulled off to drop into the container with the needle when the syringe is withdrawn from the tube.

28 Claims, 8 Drawing Sheets

U.S. PATENT DOCUMENTS

| | | | |
|---|---|---|---|
| 4,723,943 A * | 2/1988 | Spencer | 604/198 |
| 5,318,537 A * | 6/1994 | Van Der Merwe | 604/110 |
| 5,322,164 A * | 6/1994 | Richardson et al. | 206/366 |
| 5,356,383 A * | 10/1994 | Daly et al. | 604/110 |
| 5,409,112 A | 4/1995 | Sagstetter | |
| 5,445,620 A | 8/1995 | Haber et al. | |
| 5,624,400 A * | 4/1997 | Firth et al. | 604/110 |
| 5,725,501 A | 3/1998 | Lichtenberg | |
| 5,743,887 A * | 4/1998 | Brattesani | 604/192 |
| 5,947,933 A | 9/1999 | Reichenbach et al. | |
| 5,947,950 A * | 9/1999 | Shillington et al. | 604/403 |
| 5,989,226 A | 11/1999 | Hymanson | |
| 6,036,671 A | 3/2000 | Frey | |
| 6,062,001 A | 5/2000 | Kunik | |
| 6,158,314 A * | 12/2000 | Thead et al. | 83/23 |
| 6,485,469 B1 * | 11/2002 | Stewart et al. | 604/198 |
| 6,752,798 B2 * | 6/2004 | McWethy et al. | 604/506 |
| 2002/0103471 A1 | 8/2002 | Granier | |

FOREIGN PATENT DOCUMENTS

| | | |
|---|---|---|
| DE | 197 34 129 A | 2/1999 |
| EP | 0 271 793 A2 | 6/1988 |
| EP | 0 276 150 A2 | 7/1988 |
| EP | 0 441 628 A | 8/1991 |
| EP | 0 508 204 A2 | 9/1992 |
| EP | 0 515 962 A | 12/1992 |
| EP | 0 734 738 A2 | 10/1996 |
| EP | 0 787 501 A | 8/1997 |
| WO | WO 91/16089 | 10/1991 |
| WO | WO 92/15361 | 9/1992 |

* cited by examiner

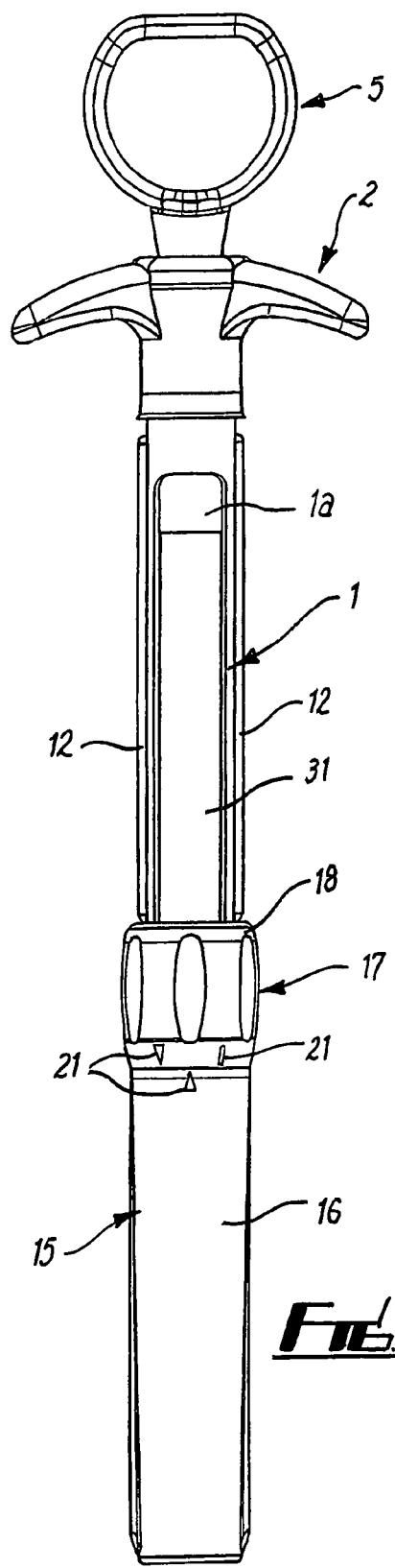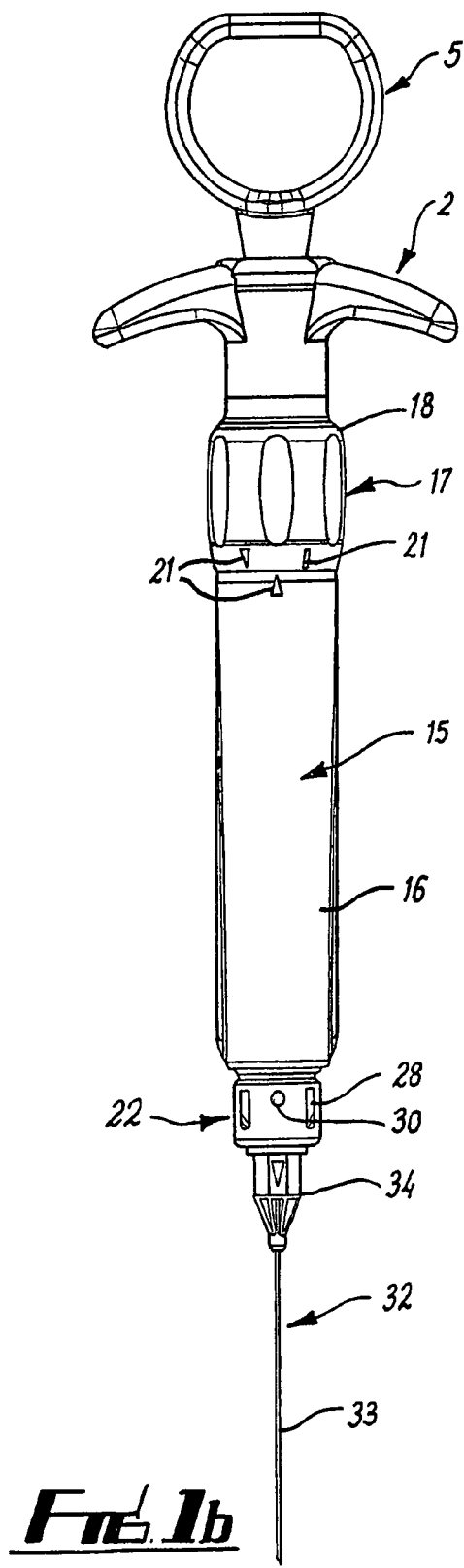
Fig. 1a
Fig. 1b

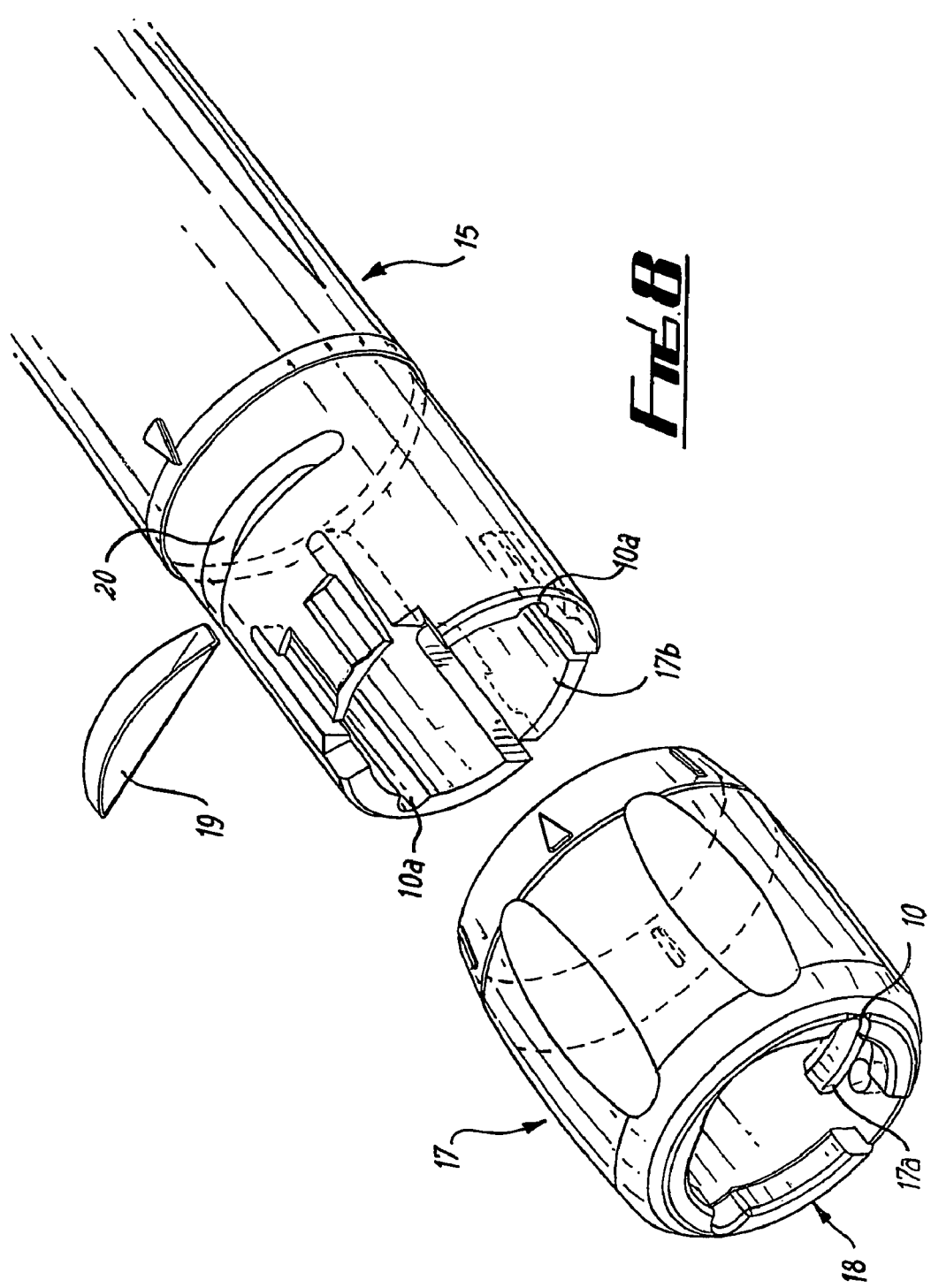

SAFETY SYRINGE WITH RE-USABLE MAIN PARTS, METHOD FOR DISPOSAL OF A NEEDLE INTO A CONTAINER AND CONTAINER FOR DISPOSABLE PARTS

BACKGROUND AND SUMMARY OF THE INVENTION

This invention relates to syringes, particularly although not exclusively for dental use, and is more particularly concerned with safe disposal of needles of such syringes.

A conventional dental syringe has a barrel with a plunger mechanism at a rear end and a threaded adaptor to receive a needle at a front end. In use a glass cartridge, which contains an injectable liquid between a rear bung and a front membrane, is inserted into the barrel. A needle having a threaded hub adjacent to its rear end is screwed onto the adaptor so that it penetrates the cartridge membrane, and the plunger mechanism is engaged with the bung at the rear end of the cartridge.

After use, the cartridge and needle are removed and discarded. For safety purposes, the needle may be deposited in a so-called 'sharps' container for safe disposal.

In order to avoid needle-stick injuries there have been various proposals for facilitating safe handling of the needle during removal and disposal.

EP 0441628A describes the use of a removal device, which may be power operated, to unscrew the needle for deposit in a sharps container without requiring direct manual contact with the needle hub or syringe adaptor. However, there is the problem of avoiding contact with the needle after use and prior to its presentation to the removal device.

U.S. Pat. No. 5,403,288 and U.S. Pat. No. 5,989,226 describe the use of a sleeve which can be fitted over the needle after use. This arrangement can give effective protection against needle stick injuries. However, there is then the problem of convenient removal and disposal of the covered needle. In each case the needle is removed together with the sleeve which is in practice requires the sleeve and possibly associated components or even the entire syringe to be disposable. Whilst disposable syringes can be acceptable there is also a requirement for syringes which have re-usable main parts.

One object of the present invention is to enable the needle of a syringe to be easily and conveniently removed for disposal whilst being effectively protected within a sleeve to prevent needle-stick injuries but without requiring disposal of the sleeve with the needle.

According to one aspect of the invention therefore there is provided a method for disposal into a container of a needle mounted on a syringe via a push-fit mounting device, the syringe having a barrel to receive a cartridge of injectable liquid with a forward end on to which the mounting device is a push-fit, a plunger mechanism connected to a rearward end of the barrel, and a sleeve mounted relative to the barrel so as to be slidable forwards to a position at which it sheaths the needle, the container having a disposal chamber with an opening thereto provided with a receiving structure having a gripper device, wherein the syringe is presented to the said receiving structure with the needle sheathed by the said sleeve, the sleeve is pushed back to expose the needle, and the mounting device passes beyond the said gripper device, and the syringe is then withdrawn so that the needle with the mounting device is pulled off the syringe barrel, for deposit in the disposal chamber, by engagement of the mounting device with the gripper device.

With this method the needle can be protected by the sleeve as it is presented to the container opening and the needle can then be removed and deposited in the container without requiring disposal of the sleeve. The needle can therefore be removed and safely discarded easily and conveniently, and the main parts of the syringe, including the sleeve, can then be re-used with a fresh needle and mounting device.

Preferably, the arrangement is such that the gripper device is a non-return device which engages behind the mounting device so as to abut a rear structure, such as a rear end edge or face, of the mounting device. Most conveniently the gripper device may be arranged to extend peripherally or circumferentially around relative to the syringe axis and thus, for example may comprise a ring of gripper fingers which are preferably resiliently deflectable to allow passage of the mounting device therethrough.

In order to ensure that the mounting device passes beyond the gripper device sufficiently to ensure that it is pulled off when the syringe is withdrawn, indicator marks or the like may be provided e.g. on the receiving structure and the syringe sleeve for alignment purposes, and/or the gripping device may be visible.

Preferably also, the arrangement may be such that the receiving structure engages a part, particularly a rear part, of the sheath, such as an enlarged rear collar, so as to push back the sheath.

In a particularly preferred embodiment the sleeve can be retained in the said forwards position by a releasable locking device, whereby this device is released after presentation of the syringe to the container opening has commenced.

The mounting device may comprise a unitary member attached, particularly permanently attached, to or integrated with the needle, as a so-called needle hub.

Alternatively the mounting device may comprise a combination of two parts comprising a needle hub integrated with the needle, and an adaptor which is a push-fit on the forward end of the barrel and to which the needle hub is connected.

Thus and in accordance with a second aspect of the invention there is provided a syringe, for use with the above method, comprising a barrel to receive a cartridge of injectable liquid, said barrel having a forward end for connection to a needle having a mounting hub, and a rearward end for connection to a plunger mechanism, a needle adaptor for mounting on the forward end of the barrel for retaining engagement with a hub of the needle to form with said hub a mounting device for the needle, and a sleeve mounted relative to the barrel so as to be slidable forwards to a position at which it is retained on the barrel but extends beyond the forward end to sheath the needle, characterised in that the needle adaptor is a push-fit on the forward end of the barrel whereby the needle and adaptor can be separated from the barrel and the sleeve by application of a linear acting removal force to the said adapter.

This arrangement allows the needle to be removed and discarded separately from the sleeve.

Also, insofar as removal requires only the application of a linear pull-off force, the needle can be detached in a particularly quick and convenient manner notwithstanding the presence of the sleeve.

With regard to the push-fit adaptor, this may be in the form of an end piece comprising a cap with one or more internal configurations such as projections which interengage surfaces or cooperable configurations of the barrel to establish a retaining e.g. tight frictional and/or snap fit.

The interengagement between the needle hub and the endpiece may be effected, in conventional manner, by screw fit engagement of an internal thread of the hub and an external threaded projecting part of the cap.

With regard to the receiving structure of the container of the above described method, this preferably comprises a passageway with an outer end through which the syringe is presented to the said opening, an inner end in communication with the said opening and having the gripper device thereat, and an abutment structure, e.g. at the outer end, for engagement with the sleeve to push this back.

Thus, and in accordance with a third aspect of the present invention there is provided a container for use with the above mentioned method comprising a disposal chamber having an opening thereto, and a receiving structure with a gripper device for holding a mounting device of a syringe needle to cause the needle to be pulled off the syringe on withdrawal thereof from the gripper device, characterised in that the receiving device comprises a passageway with an outer end through which the syringe is presented to the said opening and an inner end in communication with the said opening and having the gripper device thereat.

The gripper arrangement may be a non-return gripper which cooperates with a trailing abutment of the mounting device and thus may comprise a collar or ring having inwardly directed fingers which may deflect outwardly to allow passage of the abutment and then return inwardly to catch behind the abutment. This trailing abutment may comprise a rear end face or rim of the mounting device.

Other gripper arrangements of the nature of catch or interlock or abutment devices may also be used.

With regard to the passageway, most preferably the arrangement is such that this will receive the syringe barrel and the needle, but will not allow complete passage of the syringe sleeve whereby this is retracted as the syringe is inserted. Thus, the passageway preferably has an abutment structure arranged to engage a part e.g. an enlarged rearward end portion of the syringe sleeve. This abutment structure may be defined e.g. by a shoulder or rim at an entrance to the passageway.

The passageway may comprise a tube, such as a cylindrical tube.

The chamber may be a box capable of receiving multiple needle/mounting device combinations for disposal. Thus the chamber may be of substantially greater volume than the aforesaid passageway. This chamber may be linked to the passageway transversely to the direction in which the needle is inserted through the opening.

Alternatively to a multi-use box, the chamber may be for single use. In this case it may be of the nature of a tube with the opening through which the needle is inserted having an entrance at one end. The gripper device may also act, or be used in combination with, a holding device so that after detachment the needle/mounting device combination is held in position in the container. In this case, the tube may be open at the end remote from the needle entrance.

The sleeve of the syringe used with the above mentioned method may be mounted on the barrel so as to be slidable between rear and forward positions at which respectively the needle is arranged to be fully exposed and fully covered. At these limit positions the sleeve may be held in position frictionally and/or by a releasable catch or the like.

In one embodiment, the syringe sleeve has mounted thereon a member movable between release and locking positions whereby in the locking position cooperable configurations on the member and on the barrel interengage to prevent relative longitudinal movement of the member and the barrel and in the release position these configurations are disengaged to permit longitudinal movement.

Thus and in accordance with a further aspect of the invention there is provided a syringe for use with the above described method comprising a barrel to receive a cartridge of injectable liquid, said barrel having a forward end for connection to a needle via a push-fit mounting device, and a rearward end for connection to a plunger mechanism, and a sleeve mounted relative to the barrel so as to be slidable forwards to a position at which it is retained on the barrel but extends beyond the forward end to sheath the needle, characterised in that the syringe sleeve has mounted thereon a member movable between release and locking positions whereby in the locking position cooperable configurations on the member and on the barrel interengage to prevent relative longitudinal movement of the member and the barrel and in the release position these configurations are disengaged to permit longitudinal movement.

Preferably the movable member is provided at the rear end of the sleeve.

Conveniently, the movable member is rotatable about the axis of the barrel between locking and release positions. These positions may be limit positions which may be defined by interengagement of a peg with a slot, or by aligned markers or otherwise. The cooperable configurations may comprise a projection, particularly an elongate projection, on the member and a slot or groove in a projecting part of the barrel or vice versa.

The syringe sleeve may have a main tubular body part restrained against rotation around the barrel i.e. so that it is guided for longitudinal movement along the barrel. This may be achieved by means of a longitudinal groove or slot on one and a projection, particularly an elongate projection, which engages the groove or slot on the other and these may be aligned with the aforesaid projection and slot or groove of the movable member in the release position thereof.

The rotatable member may also comprise a tubular part or collar which is preferably of shorter length than the aforesaid main body part.

The syringe of this further aspect of the invention may have any or all of the features of the syringe of the second aspect of the invention.

BRIEF DESCRIPTION OF THE DRAWINGS

The invention will now be described further by way of example only and with reference to the accompanying drawings in which:

FIG. 1a is a plan view of one form of a syringe according to the invention with the sleeve pushed forwards;

FIG. 1b is a plan view of one form of a syringe according to the invention with the sleeve pushed rearwards;

FIG. 8 is an exploded perspective view of the rearward end of the sleeve.

DETAILED DESCRIPTION OF THE INVENTION

Figure 2:
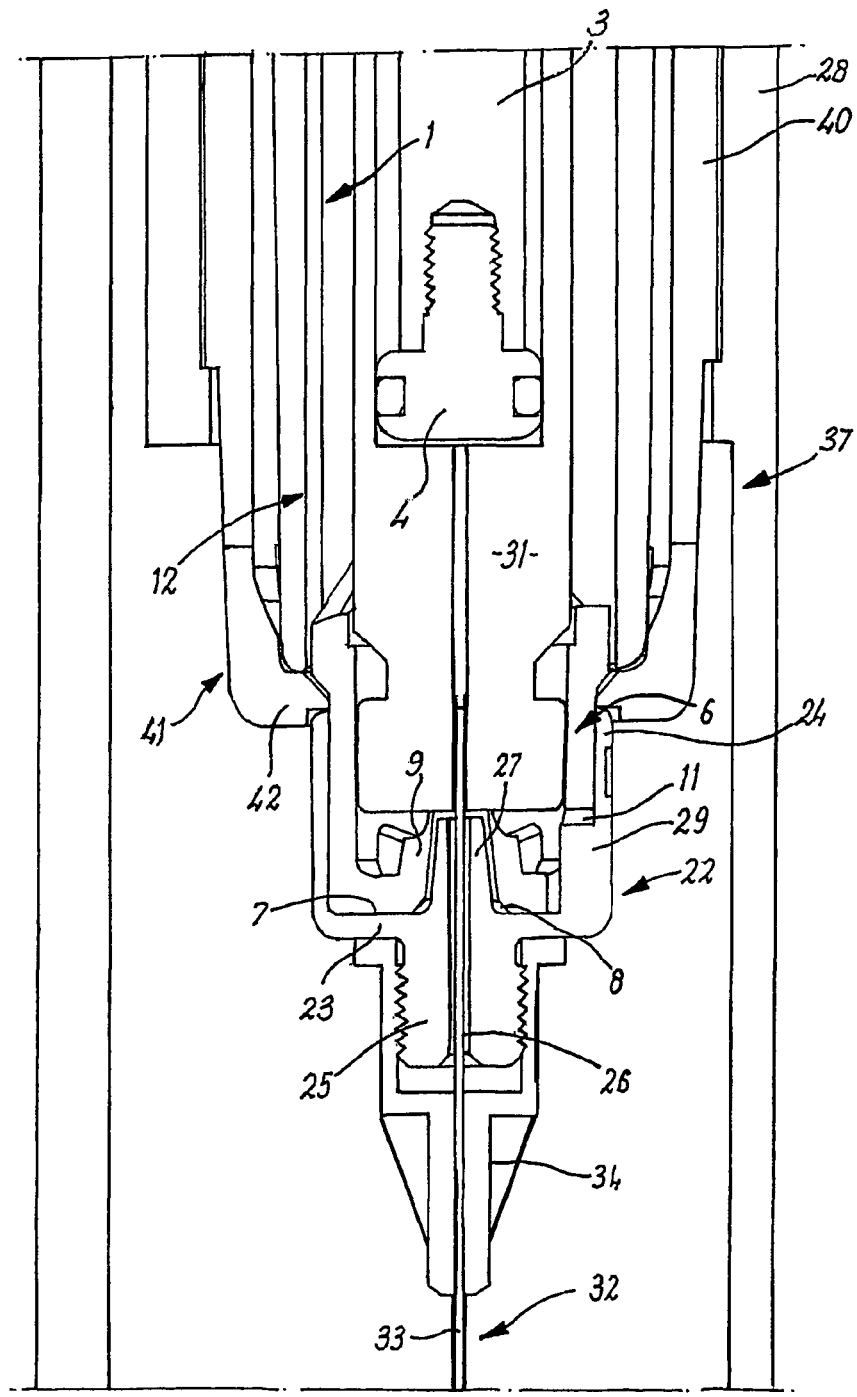
FIG. 2 is a sectional view of a forwards section of the syringe of FIG. 1, within part of a sharps container adapted for use with the syringe, with the sleeve retracted.

Referring to FIGS. 1 and 2, a dental syringe has a barrel 1 in the form of a tube of circular cross-section which is open at its rear (distal) end and closed at its forward (proximal) end and has a cut-out side opening 1a.

The barrel 1 has a finger grip structure 2 attached to the rearward open end, with a plunger 3 extending through this structure 2. The plunger 3 terminates at a forward free end with an enlarged head 4, and at a rearward end with a further finger grip 5.

At its forward end, the barrel 1 has an integral end portion 6 with a flat radially extending front end face 7 with an axial aperture 8 bounded by a rearwardly projecting tapered structure 9. There is a longitudinal slot 11 running from the end face 7.

The barrel 1, finger grip structure 2 plunger and finger grip 5 may be formed from stainless steel or plastics which can be disinfected by autoclaving or other technique.

Figure 5:
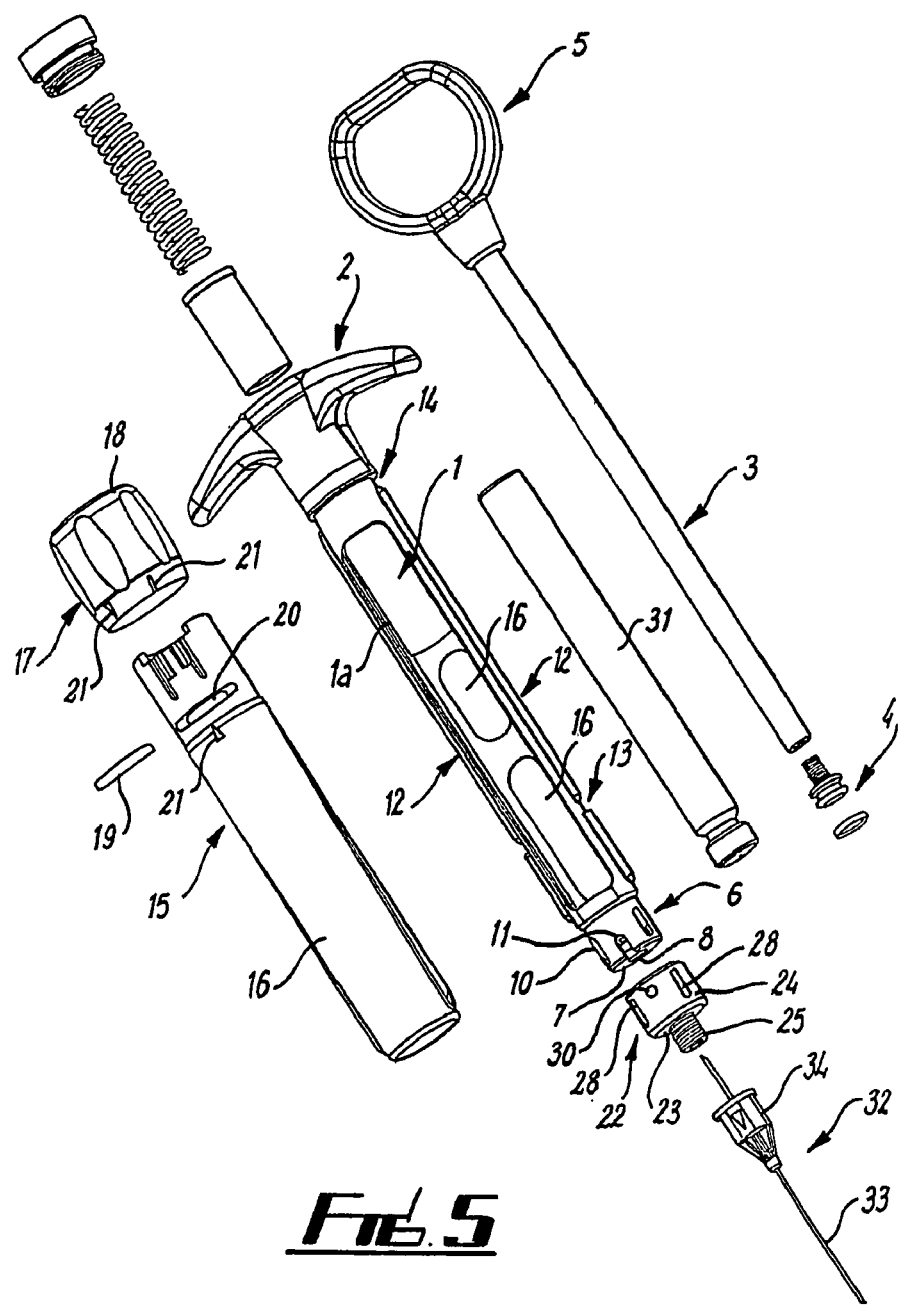
FIG. 5 is an exploded view of the syringe of FIG. 1.

As shown in FIG. 5, the barrel has diametrically opposed longitudinally extending ridges 12 with forward and rearward cut-out slots 13, 14.

Around the barrel 1 is located a sleeve 15 comprising an open ended circular cross-section tube 16 having a slightly larger diameter than that of the barrel 1. The tube 16 may be transparent or may have transparent or cut-out side sections for viewing of the barrel 1 through the side opening 1a or through windows 16 cut out of the barrel 1 opposite to the window 1a. The sleeve 15 is also formed from autoclavable material so as to be reusable e.g. stainless steel or plastics.

At a rearward end of the tube 16 there is mounted a locking member 17 in the form of an open ended tube or collar of greater diameter than the tube 16. This collar 17 is retained on the tube 16 so that a rearward end region projects beyond the end of the tube 16 and forms an inturned lip 18. A major part of the collar 17 overlies the tube 16 and is retained on the tube 16 by interengagement of an inward projection 17a on the collar 17 with a recess in a springy end part 17b of the tube 16. A curved insert 19 fits in a slot 20 in the tube 16 and projects through the tube so as to project into the cartridge slot 1a in the barrel 1. The arrangement is such that the collar 17 can rotate about the tube 16 around its axis between limit positions defined by the relative dimensions of the projection 17a and the cooperable slot in the end part 17b but is retained against longitudinal displacement on the tube 16. Markers 21 are provided on the collar 17 and on the tube 16 and are aligned respectively at the different limit positions.

The tube 16 has diametrically opposed internal grooves 10a (FIG. 8) which slidably interfit with the ridges 12 and extend along the entire length of the tube.

The sleeve 15 can slide to a rearmost position (FIG. 1b) at which its rear end abuts or in close to the finger grip structure 2 and its front end is generally level with the forward end of the barrel 1.

The sleeve 15 can slide to a forwards position (FIG. 1a) at which its rear end is slightly behind the front end of the barrel 1 and the sleeve 15 extends forwardly beyond such front end.

The interengagement between the insert 19 and the cartridge slot 1a allows longitudinal sliding until the insert abuts the forwards end of this slot 1a. The sleeve 15 is thereby prevented from displacement off the barrel 1.

The interengagement between the internal grooves of the tube 16 and the ridges 12 permits easy sliding but prevents relative rotation of the tube 16 and the barrel 1.

At the open front end of the barrel 1 there is mounted a disposable plastics end piece 22.

The end piece 22 is a one piece plastics moulding in the form of a cap of circular cross-section having a front end wall 23 and a generally cylindrical body 24 with a rear opening.

The front end wall 23 has a forward central axially extending projection 25 with an external screw thread and an internal axial through bore 26. Within the body 24 there is a rearward central axially extending tapered projection 27 also with an axial through bore.

From the end wall 23 of the cap 22 there is a longitudinal projecting ridge 29.

The end-piece 22 is a push-fit onto the end of the barrel 1 with the rearward projection 27 entering the aperture 8 and with the projection 29 in the cap 22 engaging the slot 11 in the barrel 1. This engagement is a tight fit so that the cap 22 is held securely in position. This tight fit is a function of tight wedging engagement of the cap 22 with the barrel 1. Alternatively or additionally if desired there may be a snap-fit interconnection of e.g. slots in the cap with projections on the barrel 1. A marker element 30 is provided on the cap 22 so as to help alignment of the cap projection 29 with the barrel slot 11.

The sleeve 15 can be releasably locked in the forwards position by rotation of the collar 17 to one limit position to bring projections within the collar into engagement with the gaps 13. The sleeve 15 can be released from this by rotation of the collar 17 back to its opposite limit position. In more detail the inturned rear end lip 18 of the collar 17 has diametrically opposed longitudinally extending slots 10 which in one position are aligned with the slots in the tube 16 and the ridges 12 on the barrel 1 thereby to permit longitudinal sliding with the tube 16 on the barrel 1. When the collar 17 is rotated out of this position to the opposite limit position solid parts of the lip 18 are moved into the gaps 13 in the barrel ridges 12 thereby preventing longitudinal sliding movement.

The sleeve 15 is releasably retained in the rearmost position in similar manner by movement of the solid parts of the lip 18 of the collar 17 into the gaps of the barrel ridges 14.

The syringe so far described is used with a conventional anaesthetic-filled cartridge 31 in the form of a glass tube sealed with a rear-end bung and a front end membrane, and a needle 32 comprising a stainless steel tubular member 33 with an attached hub 34, in the form of an internally threading cap, adjacent to but spaced from its rear end.

In use, with the sleeve 15 in its forwards position and the plunger 3 retracted the cartridge 31 is inserted through the side opening 1a of the barrel 1.

The plunger head 4 can then be moved forward to engage the cartridge bung.

The needle hub 34 is screwed onto the end piece 22 with the sleeve 15 in its rearward position. This causes the rear end portion of the needle 33 to pass through the bores 26 so as to be directed into position to penetrate the membrane at the front end of the cartridge 31.

The interconnection between the end piece 22 and the end portion 6 of the barrel 1 is such that the end piece 22 cannot rotate relative to the barrel e.g. when the needle is screwed into position.

The inner projecting part 27 of the end piece 22 prevents contact between the rear part of the needle 33 and the end portion 6 of the barrel 1 thereby to limit contamination. Also it guides insertion of the needle and therefore reduces the risk of bending.

The sleeve 15 can now be moved to its forward position in which it completely covers the needle 33. The sleeve 15 can be held in this forward position with the collar 17.

When required, the collar 17 can be rotated to the release position and the sleeve 15 can then be moved back to its rearward position. The needle 32 is thereby exposed for use.

After use, the sleeve 15 is again moved to its forwards position and when required the needle 32 and end piece 22 are detached together and inserted into a sharps container 35 for disposal. The spent cartridge 31 can then also be removed and discarded.

Figure 3:
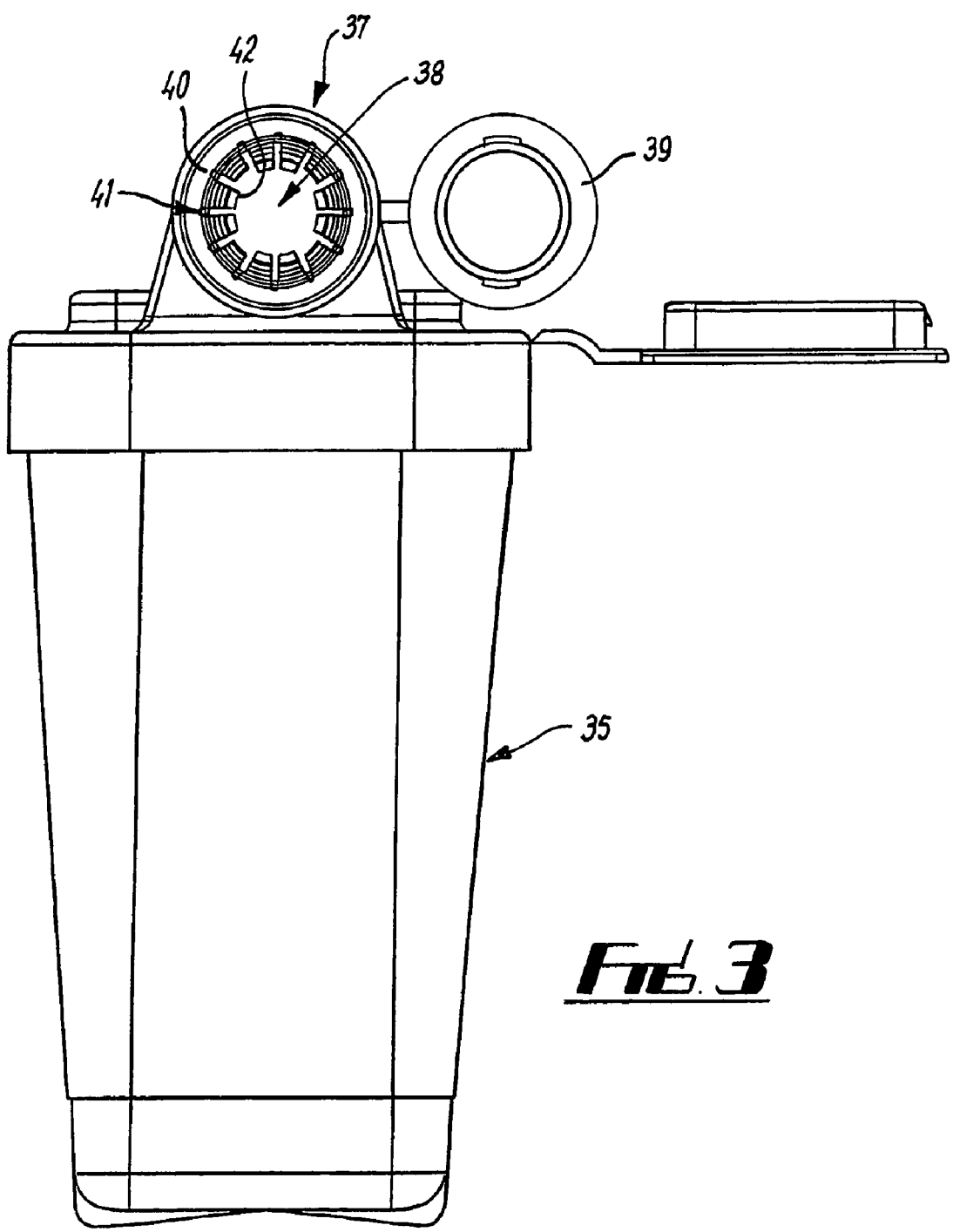
FIGS. 3 & 4 are end and top views of the sharps container, the latter Figure also showing the syringe and having a section removed.
Figure 4:
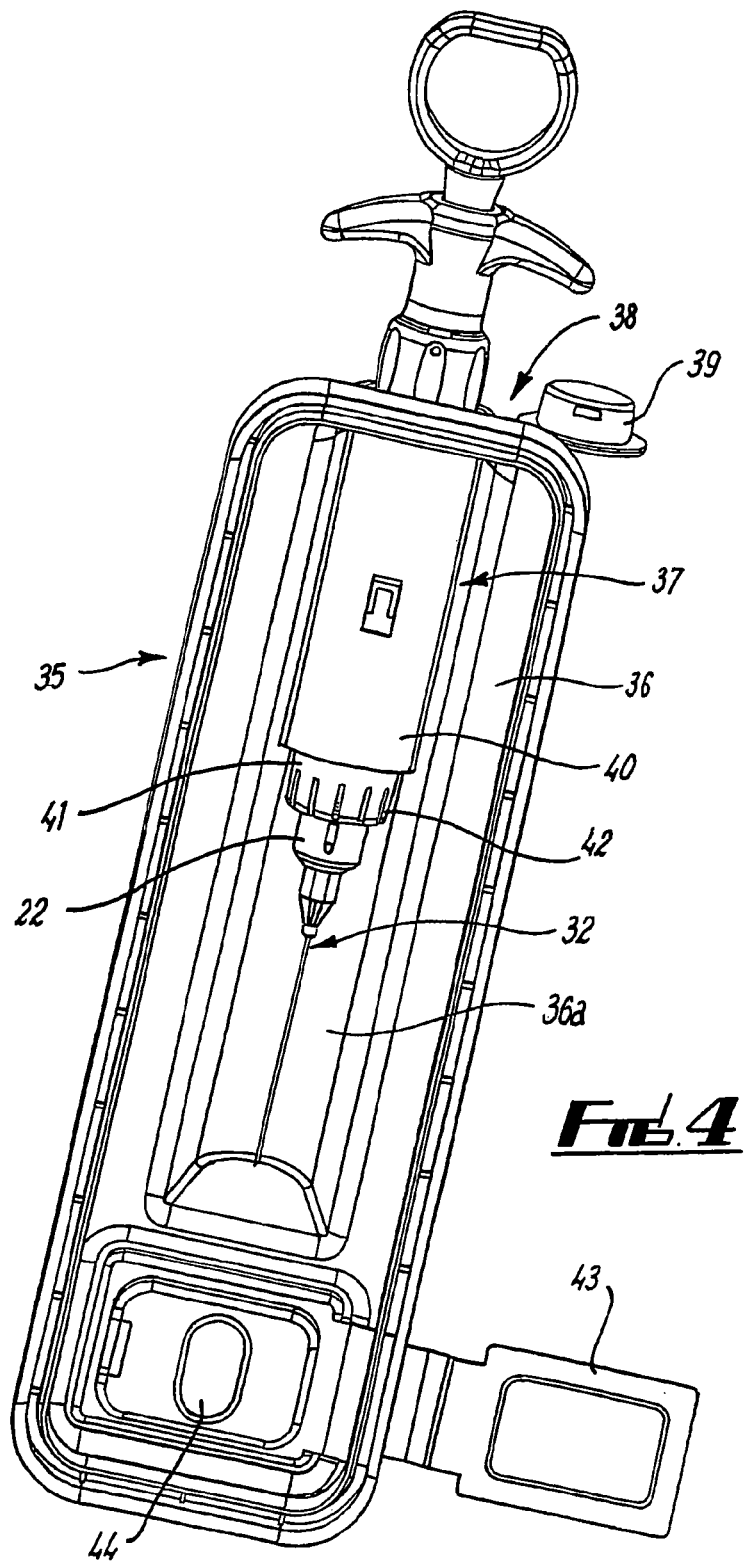

As shown is FIGS. 3 and 4, the sharps container 35 comprises a generally rectangular box structure with a top wall 36 containing an upwardly projecting integral tunnel structure 37 which has an opening 38 at one end and is closed at the opposite end. The tunnel structure 37 is open to the interior of the box structure along its lower side via an opening 36a in the wall 36.

Figure 6:
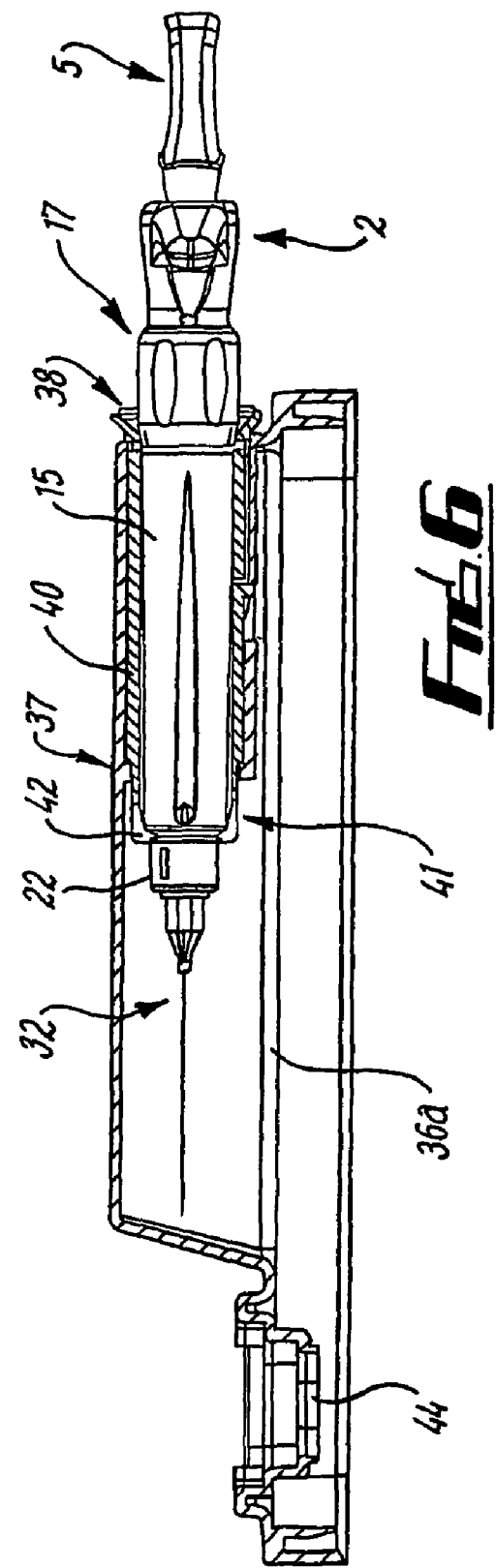
FIG. 6 is a sectional view of part of the container of FIGS. 3 and 4 with the syringe shown in full.
Figure 7:
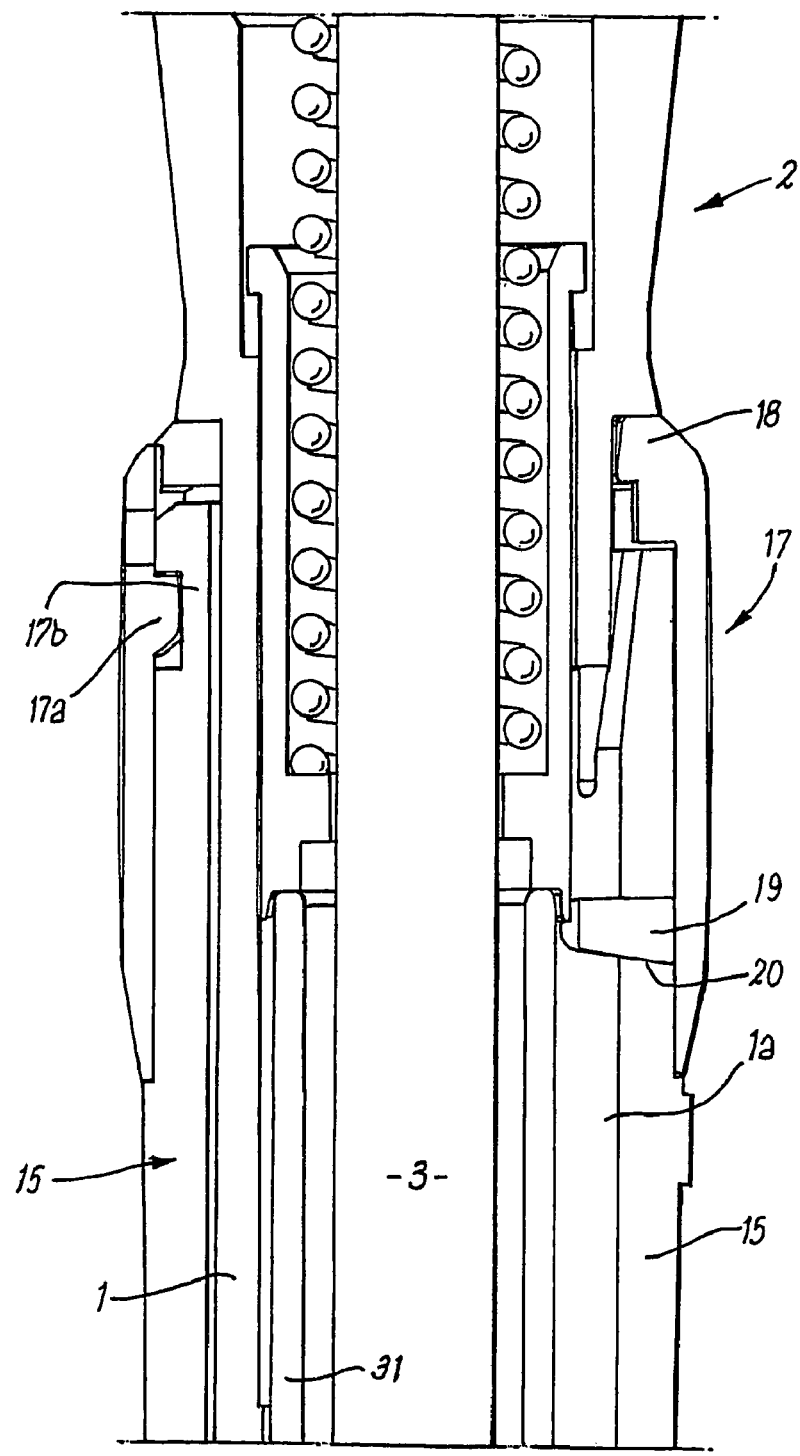
FIG. 7 is a further sectional view of a rearward detail of the syringe with the sleeve retracted.

As shown in FIG. 6 the opening 38 is bounded by an outwardly flared rim and has a detachable cap 39 for temporary closure of the opening by insertion into this rim. Within the opening 38 there is fixed a tubular structure 40, defined by a removable snap-in sleeve within a retaining structure 28 of the tunnel structure 37, which is open at both ends and extends from the periphery of the opening 38 inwardly part way along the tunnel structure 37.

Within the tubular structure 40 there is fixed a collar 41 which projects beyond the innermost end of the structure 40 and at such projecting end has a ring of resiliently deflectable fingers 42 which project axially into the tunnel structure 37 away from the opening 38 and are inclined inwardly towards the axis of the tubular structure 40.

The tunnel structure 37 extends only partially along the top wall 36 of the container 35. Beyond the closed end of the tunnel structure 37 there is a further opening 44 in the top wall 36, which can be temporarily closed with a cover flap 43, to receive spent cartridges 31.

Internally, the box structure 35 has a compartment which receives the used needles 32 and spent cartridges 31. The openings 36a and 44 communicate with this.

The syringe with a used needle in position is presented to the opening 38 with the sleeve 15 fully covering the needle 32 and locked in position.

The internal diameter of the tubular structure 40 is large enough to permit entry of the tube 16 of the sleeve 15 and is approximately the same length as such tube 16. However, the internal diameter is not wide enough to receive the enlarged collar 17. The syringe can therefore be pushed in until the collar 17 reaches the rim around the opening 38. The collar 17 is then manually rotated to the release position and the syringe in pushed further in.

At the innermost end of the tubular structure 40, a shoulder is defined between the tubular structure 40 and the collar 41, the collar being of slightly smaller diameter than the tubular structure 40.

As the syringe is pushed through the opening 38 the sleeve 15 is pushed back on the barrel 1 by engagement of the rim around the opening 38 with the collar 17 and the needle 32 and end-piece 22 ultimately pass through the collar 41 to a position beyond the free ends of the fingers 42. The fingers 42 deflect outwardly to permit this and then close inwardly behind the end of the end piece 22 so as to grip the barrel 1 and engage the rim of the rear of the end piece 22, as indicated in FIG. 2.

A marker or the like may be provided to indicate when the syringe is fully inserted to the extent that the fingers are locked behind the end piece 22.

Withdrawal of the syringe using the finger grip structure 2 now causes the end piece 22 with the needle 32 to be pulled off the syringe barrel 1 and to fall downwardly through the opening 36a into the container 35. The cartridge 31 can now be removed and inserted through the opening 44 into the container 35.

The interfit between the barrel 1 and the cap 22 is such as to ensure secure retention in normal use but so as to permit release and pull-off of the cap 22 when a suitable force, acting longitudinally of the syringe axis is applied.

The main part of the syringe, namely the barrel 1, finger grip structure 2, plunger 3 and finger grip 5, and sleeve 15 can now be disinfected and re-used with a fresh end piece 22, needle 32 and cartridge 31.

With this arrangement, needle stick injuries can be avoided with a syringe arrangement which permits retention for reuse of main parts of the syringe whilst facilitating ready removal and disposal of a used needle. The arrangement of the syringe is also such as to ensure safety during use.

It is of course to be understood that the invention in not intended to be restricted to details of the above embodiment which are described by way of example only.

Thus, for example, instead of using a conventional needle 32 with its threaded hub 34 and the separate end piece 22 these may be integrated i.e. such that the needle has an integral hub which, like the end piece 22, is a push fit on the end portion 6 of the barrel 1.

The invention claimed is:

1. A method for disposal into a container of a needle mounted on a syringe via a push-fit mounting device, said syringe having a barrel to receive a cartridge of injectable liquid with a forward end onto which the mounting device is push-fit, a plunger mechanism connected to a rearward end of the barrel, and a sleeve mounted relative to the barrel so as to be slidable forwards to a position at which it sheaths the needle, and said container having a disposal chamber with an opening thereto provided with a receiving structure having a gripper device, said method comprising:

presenting the syringe to the receiving structure with the needle sheathed by the sleeve, pushing back the sleeve to expose the needle, wherein the receiving structure engages a part of the sleeve so as to push back the sleeve, and passing the mounting device beyond the gripper device, and withdrawing the syringe so that the needle with the mounting device is pulled off the syringe barrel, for deposit in the disposal chamber, by engagement of the mounting device with the gripper device.

2. A method according to claim 1 wherein the gripper device is a non-return device which engages behind the mounting device so as to abut a rear structure of the mounting device.

3. A method according to claim 1 wherein the sleeve is retained in the forward position by a releasable locking device which is released after presentation of the syringe to the container opening has commenced.

4. A syringe for use with the method of claim 1 comprising:

a barrel to receive a cartridge of injectable liquid, said barrel having a forward end for connection to a needle having a mounting hub, and a rearward end for connection to a plunger mechanism, a needle adaptor for mounting on the forward end of the barrel for retaining engagement with the hub of the needle to form with said hub a mounting device for the needle, and a sleeve mounted relative to the barrel so as to be slidable forwards to a position at which it is retained on the barrel but extends beyond the forward end to sheath the needle, wherein the needle adaptor is push-fit on the forward end of the barrel whereby the needle and adaptor can be separated from the barrel and the sleeve by application of a linear acting removal force to the adaptor.

5. A syringe according to claim 4 wherein the adaptor comprises a cap which has one or more internal configurations which interengage the barrel to establish a retaining fit.

6. A syringe according to claim 5 wherein the cap has an externally threaded projecting part for retaining engagement with an internally threaded needle hub.

7. A container for use with the method of claim 1 comprising:
- a disposal chamber having an opening thereto, and
- a receiving structure with a gripper device for holding a mounting device of a syringe needle to cause the needle to be pulled off the syringe on withdrawal thereof from the gripper device,
- wherein the receiving structure comprises a passageway with an outer end through which the syringe is presented to the opening and an inner end in communication with the opening and having the gripper device at said inner end.

8. A container according to claim 7 wherein the gripper device is a non-return gripper which cooperates with a trailing abutment of the mounting device.

9. A container according to claim 8 wherein the gripper device comprises a collar or ring having inwardly directed fingers.

10. A container according to claim 9 wherein the fingers are resiliently deflectable.

11. A container according to claim 7 wherein the passageway has an abutment structure arranged to engage a part of the syringe sleeve.

12. A container according to claim 11 wherein said part comprises an enlarged rearward end portion of the sleeve.

13. A container according to claim 11 wherein the abutment structure comprises a shoulder or lip at an entrance to the passageway.

14. A container according to claim 7 wherein the passageway comprises a tube.

15. A container according to claim 7 wherein the chamber is of substantially greater volume than the passageway.

16. A container according to claim 15 wherein the chamber is linked transversely to the passageway.

17. A syringe for use with the method of claim 1 comprising:
- a barrel to receive a cartridge of injectable liquid, said barrel having a forward end for connection to a needle via a push-fit mounting device, and a rearward end for connection to a plunger mechanism, and
- a sleeve mounted relative to the barrel so as to be slidable forwards to a position at which the sleeve is retained on the barrel but extends beyond the forward end to sheath the needle,
- wherein the syringe sleeve has mounted thereon a member movable relative to the sleeve between release and locking positions whereby in the locking position cooperable configurations on the movable member and the barrel interengage to prevent relative longitudinal movement of the sleeve, the movable member and the barrel and in the release position these configurations are disengaged to permit longitudinal movement.

18. A syringe according to claim 17 wherein the movable member is provided at the rear end of the sleeve.

19. A syringe according to claim 17 wherein the movable member is rotatable about the axis of the barrel between locking and release positions.

20. A syringe according to claim 19 wherein the positions are limit positions.

21. A syringe according to claim 17 wherein the cooperable configurations comprise a projection on one of the member and the barrel and a slot or a groove on the other thereof.

22. A syringe according to claim 17 wherein the sleeve has a main tubular body part restrained against rotation around the barrel.

23. A syringe according to claim 22 there is provided a longitudinal groove or slot on one of the sleeve and the barrel and a projection on the other thereof whereby the projection engages the slot or groove to restrain the tubular body part as aforesaid.

24. A syringe according to claim 21 wherein the slot or groove and projection of the sleeve and barrel are aligned with the slot or groove and projection of the movable member and the barrel in the release position.

25. A syringe according to claim 17 wherein the movable member comprises a collar.

26. A syringe according to claim 17 wherein the sleeve is lockable in the forwards position thereof.

27. A syringe according to claim 17 wherein the sleeve is lockable in a rearwards position at which it is retracted away from the needle.

28. The method of claim 1, wherein the container is disposable.

* * * * *